(12) United States Patent
Kaito et al.

(10) Patent No.: US 8,274,063 B2
(45) Date of Patent: Sep. 25, 2012

(54) COMPOSITE FOCUSED ION BEAM DEVICE, PROCESS OBSERVATION METHOD USING THE SAME, AND PROCESSING METHOD

(75) Inventors: Takashi Kaito, Chiba (JP); Yoshitomo Nakagawa, Chiba (JP); Junichi Tashiro, Chiba (JP); Yasuhiko Sugiyama, Chiba (JP); Toshiaki Fujii, Chiba (JP); Kazuo Aita, Chiba (JP); Takashi Ogawa, Chiba (JP)

(73) Assignee: SII NanoTechnology Inc. (JP)

( * ) Notice: Subject to any disclaimer, the term of this patent is extended or adjusted under 35 U.S.C. 154(b) by 198 days.

(21) Appl. No.: 12/733,091

(22) PCT Filed: Aug. 6, 2008

(86) PCT No.: PCT/JP2008/064123
§ 371 (c)(1),
(2), (4) Date: Mar. 19, 2010

(87) PCT Pub. No.: WO2009/020151
PCT Pub. Date: Feb. 12, 2009

(65) Prior Publication Data
US 2010/0288924 A1    Nov. 18, 2010

(30) Foreign Application Priority Data
Aug. 8, 2007    (JP) .................................. 2007-207098

(51) Int. Cl.
*H01J 49/00*    (2006.01)
(52) U.S. Cl. ............. 250/492.21; 250/492.1; 250/492.3; 250/493.1
(58) Field of Classification Search .............. 250/423 R, 250/492.21, 306, 309
See application file for complete search history.

(56) References Cited

U.S. PATENT DOCUMENTS

| | | | | | |
|---|---|---|---|---|---|
| 4,874,460 | A | * | 10/1989 | Nakagawa et al. ............. | 216/61 |
| 5,023,453 | A | * | 6/1991 | Adachi et al. .................... | 850/9 |
| 5,149,973 | A | * | 9/1992 | Morimoto ................... | 250/492.2 |
| 5,306,663 | A | * | 4/1994 | Morimoto ....................... | 438/641 |
| 5,504,340 | A | * | 4/1996 | Mizumura et al. ........ | 250/492.21 |
| 5,525,806 | A | * | 6/1996 | Iwasaki et al. ........... | 250/492.21 |
| 5,583,344 | A | * | 12/1996 | Mizumura et al. ....... | 250/492.21 |
| 5,825,035 | A | * | 10/1998 | Mizumura et al. ........ | 250/423 R |

OTHER PUBLICATIONS

Abstract, publication No. 06-260129, publication date Sep. 16, 1994.
Abstract, publication No. 04-076437, publication date Mar. 11, 1992.

* cited by examiner

*Primary Examiner* — Jack Berman
*Assistant Examiner* — Johnnie L Smith
(74) *Attorney, Agent, or Firm* — Adams & Wilks

(57) ABSTRACT

A composite focused ion beam device has a first ion beam irradiation system that irradiates a first ion beam for processing a sample and a second ion beam irradiation system that irradiates a second ion beam for processing or observing the sample. The first ion beam irradiation system has a plasma type gas ion source that generates first ions for forming the first ion beam, each of the first ions having a first mass. The second ion beam irradiation system has a gas field ion source that generates second ions for forming the second ion beam. Each of the second ions has a second mass smaller than that of the first mass.

20 Claims, 10 Drawing Sheets

COMPOSITE FOCUSED ION BEAM DEVICE, PROCESS OBSERVATION METHOD USING THE SAME, AND PROCESSING METHOD

CROSS-REFERENCE TO RELATED APPLICATIONS

This application is a U.S. national stage application of copending International Application No. PCT/JP2008/064123, filed Aug. 6, 2008, claiming a priority date of Aug. 8, 2007, and published in the non-English language.

BACKGROUND OF THE INVENTION

1. Technical Field

The present invention relates to a composite focused ion beam device, a process observation method using the same, and a processing method.

Priority is claimed on Japanese Patent Application No. 2007-207098, the content of which is incorporated herein by reference.

2. Background Art

Conventionally, as a composite focused ion beam device, a composite device including an ion beam irradiation system having a liquid gallium ion source and an ion beam irradiation system having an argon gas ion source is known (for example, see Patent Document 1). In addition, a device which includes an ion beam irradiation system and an electron beam irradiation system and processes a sample by the ion beam irradiation system while observing an sample using the electron beam irradiation system is known (for example, see Patent Document 2).

According to the focused ion beam device described in Patent Document 1, cleaning using an argon ion beam is performed after processing a sample using a gallium ion beam such that gallium ions injected into the sample can be removed. Meanwhile, according to the focused ion beam device described in Patent Document 2, a thin-film sample for Transmission Electron Microscope (TEM) observation can be processed while checking a finishing state by Scanning Electron Microscope (SEM; electron beam irradiation system) observation.

However, if the gallium ion beam is used for processing the sample, the implantation of a metallic ion to the sample cannot be avoided. In the focused ion beam device described in Patent Citation 1, the gallium ion can be removed, but much time is consumed by the removal process.

Patent Citation 1: Japanese Unexamined Patent Application Publication No. 6-260129
Patent Citation 2: Japanese Unexamined Patent Application Publication No. 4-076437

SUMMARY OF THE INVENTION

The present invention is contrived to solve the above-mentioned problems. An object of the present invention is to provide a composite focused ion beam device capable of rapidly processing a sample such as a silicon wafer without contamination so as to realize high-resolution observation and fine processing, a process observation method using the same, and a processing method.

In order to solve the above-described problems, according to an aspect of the present invention, there is provided a composite focused ion beam device including: a first ion beam irradiation system including a plasma type gas ion source for generating a first ion; and a second ion beam irradiation system including a gas field ion source (also referred to as an electric field ionized gas ion source) for generating a second ion, wherein a beam diameter of the second ion beam emitted from the second ion beam irradiation system is smaller than that of the first ion beam emitted from the first ion beam irradiation system.

According to this configuration, since two types of ion beam irradiation systems are included, it is possible to process the sample using one ion beam irradiation system while observing the sample using the other ion beam irradiation system. In particular, since the beam diameter of the second ion beam irradiation system including the gas field ion source can be narrowed, high-resolution observation is possible.

Since both ion beam irradiation systems use the gas ion source, the sample is not contaminated by the irradiation of the ion beam. Accordingly, even after the sample during the process of manufacturing a semiconductor device is processed and observed by the composite converted ion beam device of the present invention, the sample can be returned to the processing and thus a product is not wasted.

According to another aspect of the present invention, there is provided a composite focused ion beam device including: a first ion beam irradiation system including a plasma type gas ion source for generating a first ion; and a second ion beam irradiation system including a gas field ion source for generating a second ion, wherein a mass of the second ion is smaller than that of the first ion.

Since the second ion beam irradiation system using the second ion having the mass smaller than that of the first ion is included, it is possible to suppress sample sputtering by the irradiation of the ion beam at the time of observation. The first ion beam having a large mass is suitable for processing because sputtering efficiency is high.

An electron beam irradiation system may be further included.

According to this configuration, since the sample can be observed using the electron beam irradiation system as an observation device, it is possible to process the sample to various processing forms while properly selecting the first ion beam irradiation system and the second ion beam irradiation system and to check the finishing state of the processing by the electron beam irradiation system. Accordingly, it is possible to obtain a composite focused ion beam device capable of efficiently processing a sample with high precision.

The first ion beam irradiation system and the second ion beam irradiation system may be disposed such that the first ion beam and the second ion beam cross at an acute angle.

By disposing the first and second ion beam irradiation systems in this manner, it is possible to obtain a composite focused ion beam device which can be suitably used for an application for processing a sample while observing the sample.

A sample pedestal for supporting a sample to which the first and second ion beams are irradiated may be included, and the second ion beam irradiation system may be disposed on the upper side of the sample pedestal in a vertical direction and the first ion beam irradiation system may be disposed obliquely to the vertical direction. By disposing the second ion beam irradiation system used for high-resolution observation in the vertical direction of the sample pedestal, it is possible to improve quake resistance.

If the sample has a small dimension of several mm, the first and second ion beam irradiation systems are disposed such that the first and second ion beams are substantially orthogonal to each other. By this configuration, since the ion beam can be vertically irradiated from one ion beam irradiation system to the processed portion of the sample using the other ion beam irradiation system, in particular, it is possible to obtain a configuration suitable for an application requiring observation during processing.

If both the first and second ion beams are used for processing, the first and second ion beam irradiation systems may be disposed such that the first and second ion beams are substantially parallel to each other.

By this configuration, after rough processing is performed using the first ion beam, a stage is moved to a position where the second ion beam is irradiated and finishing processing is performed.

A sample pedestal for supporting a sample to which the first and second ion beams are irradiated may be included, and the sample pedestal may be moved freely between a first support position where the first ion beam is irradiated to the sample in a substantially vertical direction and a second support position where the second ion beam is irradiated to the sample in the substantially vertical direction. That is, in detail, the sample pedestal is horizontally moved such that the ion beams are switched.

An electron beam irradiation system for irradiating an electron beam to the sample supported at the second position may be included.

If the electron beam irradiation system is disposed at the second ion beam irradiation system side for narrowing the beam diameter, while both beams are simultaneously irradiated or the beam is switched, it is possible to observe the sample using the electron beam after finishing processing of the sample using the second ion beam. Accordingly, it is possible to check a region to be observed with certainty.

The device having this configuration is suitable for the manufacture of a flake sample for TEM observation. Since processing is performed under SEM monitoring, a flake position can be made precise and observation damage can be avoided.

The gas field ion source may include an emitter, an extraction electrode having an opening facing a front end of the emitter, and a gas supply unit for supplying gas which becomes the second ion.

By the gas field ion source having this configuration, it is possible to stably form an ion beam having a small beam diameter.

The second ion may be a helium ion.

By this configuration, a composite focused ion beam device including the second ion beam irradiation system capable of obtaining a sample image without sample sputtering is produced.

The first ion may be one type or more of rare gas ions selected from neon, argon, xenon and krypton.

By this configuration, it is possible to stably obtain the first ion beam which does not contaminate the sample even when being irradiated.

A detection device for detecting at least one of a secondary charged particle generated from the sample by the irradiation of the first ion or the second ion and a charged particle transmitted through the sample and an image display device for displaying an image of the sample based on an output of the detection device may be included.

By this configuration, it is possible to obtain a composite focused ion beam device capable of observing a sample image by the irradiation of an ion beam.

The detection device may include at least one of an electron detector, an ion detector, and a transmitted charged particle detector. That is, devices for detecting any one of a secondary electron, a secondary ion and a transmitted charged particle generated from the sample by the irradiation of the ion beam may be included.

The detection device may include a first ion detector for detecting a secondary ion generated by the irradiation of the first ion generated from the first ion beam irradiation system and a second ion detector for detecting a reflection ion generated from the second ion beam irradiation system and reflected by collision of the second ion lighter than the first ion with the sample.

According to this configuration, it is possible to acquire an image obtained from the secondary ion and an image obtained from the reflection ion. To this end, for example, during processing, it is possible to simultaneously acquire the image of the sample surface of the processed portion of the sample and the image of the sample section of the processed portion.

A gas gun for supplying functional gas for deposition or etching may be included in the vicinity of the sample to which the first and second ion beams are irradiated.

According to this configuration, it is possible to obtain a composite focused ion beam device capable of rapidly and easily performing forming of a structure by gas assisted deposition and processing of the sample by gas assisted etching.

According to another aspect of the present invention, there is provided a processing observation method of irradiating an ion beam to a sample, the method including the steps of: irradiating a first ion beam from a first ion beam irradiation system including a plasma type gas ion source for generating a first ion to the sample so as to process the sample; and irradiating a second ion beam from a second ion beam irradiation system, which includes a gas field ion source for generating a second ion and emits an ion beam having a beam diameter smaller than that of the first ion beam, to the sample so as to observe the sample.

According to this processing observation method, it is possible to rapidly and efficiently perform the processing of the sample using the first ion beam irradiation system which has a relatively large beam diameter and does not include a metallic ion without contaminating the sample and to perform observation while avoiding damage or contamination of the sample using the second ion beam irradiation system having a small beam diameter. Since the metallic ion is not irradiated, it is possible to perform processing observation while avoiding the contamination of the sample.

According to another aspect of the present invention, there is provided a processing observation method of irradiating an ion beam to a sample, the method including the steps of: irradiating a first ion beam from a first ion beam irradiation system including a plasma type gas ion source for generating a first ion to the sample so as to process the sample; and irradiating a second ion beam from a second ion beam irradiation system, which includes a gas field ion source for generating a second ion having a mass smaller than that of the first ion, to the sample so as to observe the sample.

According to this processing observation method, it is possible to rapidly and efficiently perform the processing of the sample using the first ion beam irradiation system using the first ion having a relatively large mass and to perform observation while avoiding damage or contamination of the sample using the second ion beam irradiation system using the second ion having a small mass. Since the metallic ion is not irradiated, it is possible to perform processing observation while avoiding the contamination of the sample.

The step of irradiating the first ion beam so as to process the sample and the step of irradiating the second ion beam so as to observe the sample may be simultaneously performed.

According to this configuration, when the processing is performed by irradiating the first ion beam, it is possible to perform the observation of the processed portion in real time and to improve processing precision.

The step of irradiating the second ion beam to the sample while supplying gas to an ion beam irradiation position of the sample so as to process the sample may be included.

When the sample is processed using the second ion beam irradiation system, since fine processing is possible compared with the case where the first ion beam irradiation system is used, it is possible to easily perform fine processing with high precision by a combination of the processing using the first ion beam irradiation system and the processing using the second ion beam irradiation system and to perform processing observation with more certainty.

According to another aspect of the present invention, there is provided a processing method of irradiating an ion beam to a sample, the method including the steps of: irradiating a first ion beam from a first ion beam irradiation system including a plasma type gas ion source for generating a first ion to the sample so as to perform rough processing with respect to the sample; and irradiating a second ion beam from a second ion beam irradiation system, which includes a gas field ion source for generating a second ion and emits an ion beam having a beam diameter smaller than that of the first ion beam, to a portion of a rough-processed portion of the sample so as to perform finishing processing with respect to the sample.

According to this processing method, since the sample is processed using the combination of the first ion beam irradiation system and the second ion beam irradiation system having different beam diameters, it is possible to efficiently perform high-precision processing. In addition, since the metal ion is not irradiated, it is possible to perform processing while avoiding the contamination of the sample.

According to another aspect of the present invention, there is provided a processing method of irradiating an ion beam to a sample, the method including the steps of: irradiating a first ion beam from a first ion beam irradiation system including a plasma type gas ion source for generating a first ion to the sample so as to perform rough processing with respect to the sample; and irradiating a second ion beam from a second ion beam irradiation system, which includes a gas field ion source for generating a second ion having a mass smaller than that of the first ion, to a portion of a rough-processed portion of the sample so as to perform finishing processing with respect to the sample.

According to this processing method, since the sample is processed using the combination of the first ion beam irradiation system and the second ion beam irradiation system having different masses, it is possible to efficiently perform high-precision processing using a difference between both processing performances. In addition, since the metal ion is not irradiated, it is possible to perform processing while avoiding the contamination of the sample.

The step of performing the finishing processing may be performed while observing the processed portion by irradiating an electron beam to the processed portion by the second ion beam. Accordingly, since the processing can be performed while checking the finishing state, it is possible to perform the processing with high precision.

The step of irradiating the first ion beam to the sample so as to process the sample and the step of irradiating the second ion beam to at least a portion of the processed portion of the sample by the irradiation of the first ion beam so as to perform the after-processing with respect to the sample may be simultaneously performed.

In this case, it is possible to simultaneously perform the rough processing by the irradiation of the first ion beam and the finishing processing by the irradiation of the second ion beam and to further improve processing efficiency.

According to the present invention, it is possible to provide a composite focused ion beam device capable of performing super-high-resolution SIM observation as compared with the related art and of performing processing without contaminating a sample.

According to the present invention, it is possible to provide a processing observation method capable of performing high-resolution observation while processing a sample, and a device and method capable of performing processing without contaminating the sample. Since a metallic ion is not irradiated to the sample, metallic contamination of the sample does not occur and a silicon wafer or the like which is provided to processing observation or the like can be returned to a line.

EXPLANATION OF REFERENCE

10: FIRST ION BEAM IRRADIATION SYSTEM
10A: FIRST ION BEAM
11: GAS GUN
13: VACUUM CHAMBER
14: SAMPLE PEDESTAL
15: SAMPLE HOLDER
18: SECONDARY CHARGED PARTICLE DETECTOR
19: TRANSMITTED CHARGED PARTICLE DETECTOR
20: SECOND ION BEAM IRRADIATION SYSTEM

20A: SECOND ION BEAM
21: GAS FIELD ION SOURCE
21a: ION GENERATION CHAMBER
25: ION OPTICAL SYSTEM
26: GAS SUPPLY SOURCE
26a: GAS INTRODUCTION PIPE
30: CONTROL DEVICE
34: TYPE GAS ION SOURCE
35: ION OPTICAL SYSTEM
38: DISPLAY DEVICE
50: ELECTRON BEAM IRRADIATION SYSTEM
50A: ELECTRON BEAM
Wa: SAMPLE
Wb: SAMPLE
100, 100A, 200A, 200B: COMPOSITE FOCUSED ION BEAM DEVICE

DETAILED DESCRIPTION OF THE PREFERRED EMBODIMENTS

Hereinafter, the embodiments of a composite focused ion beam device of the present invention will be described with reference to the drawings.

Figure 1:
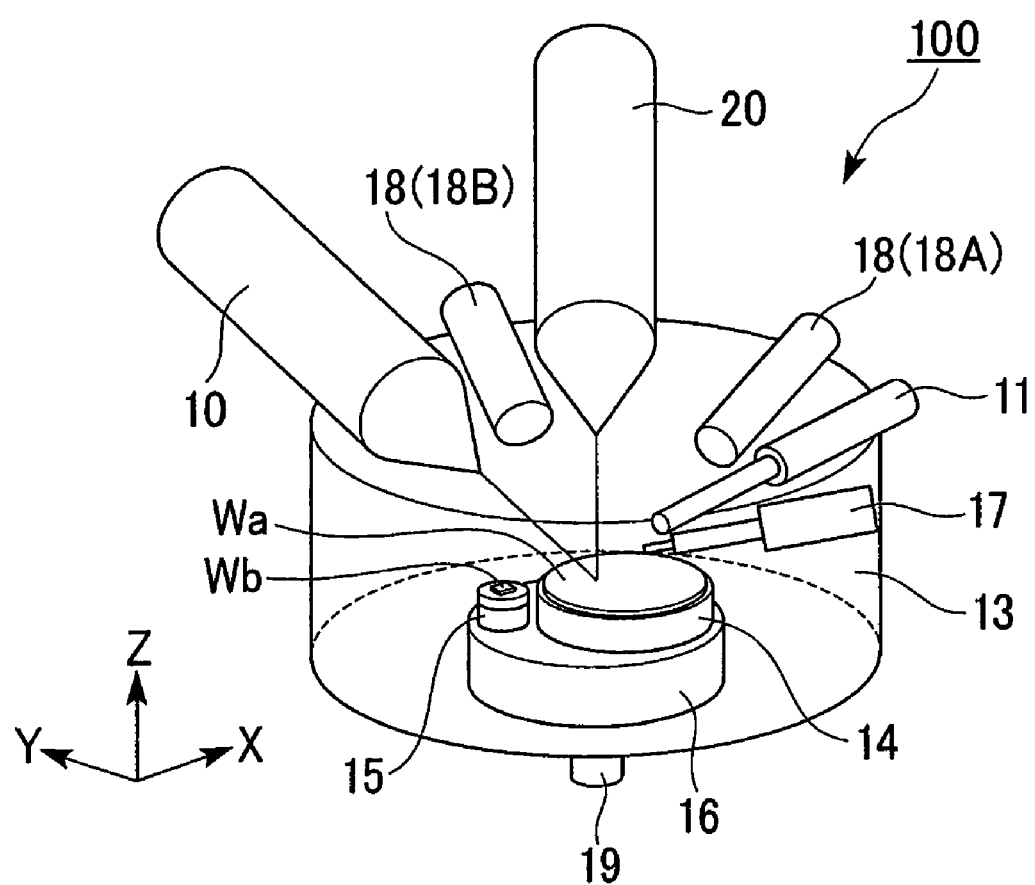
FIG. 1 is a schematic configuration diagram of a composite focused ion beam device according to a first embodiment.
Figure 2:
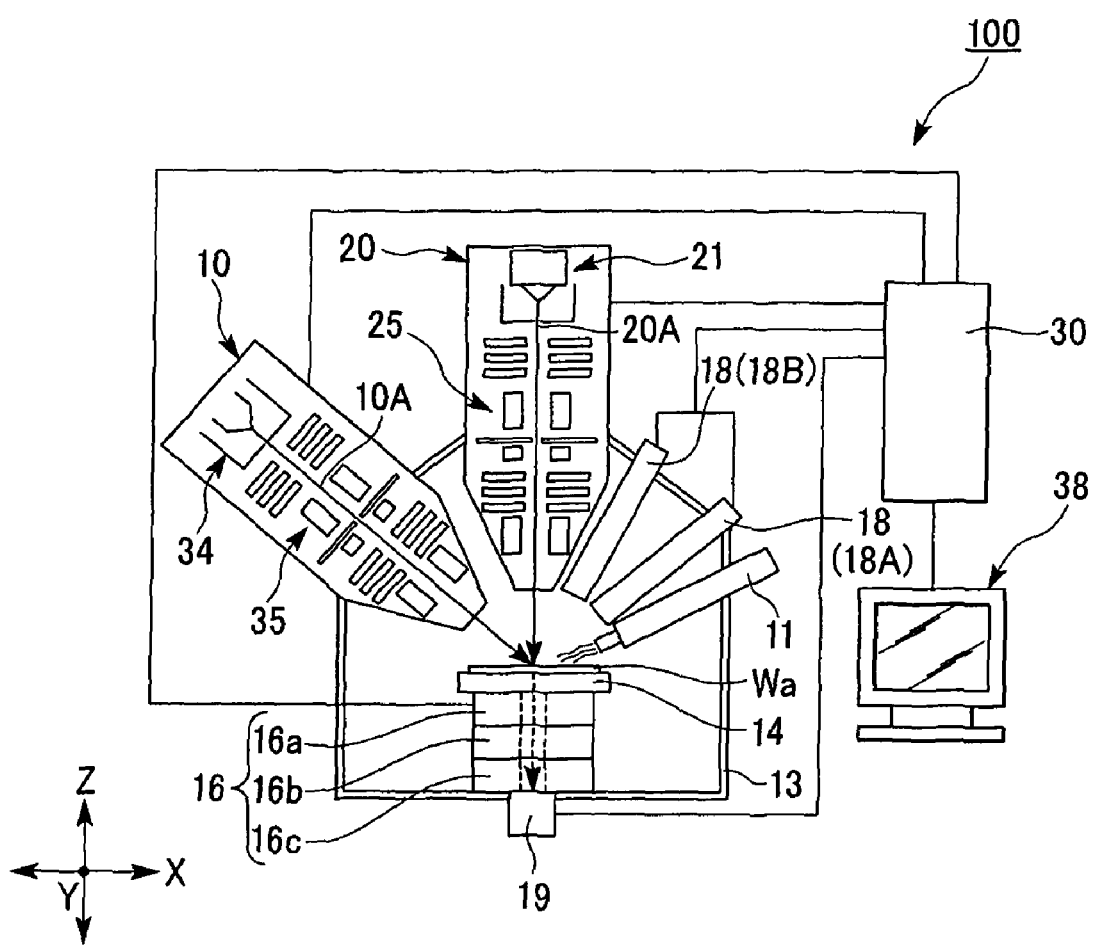
FIG. 2 is a schematic cross-sectional view of the composite focused ion beam device according to the first embodiment.

FIG. 1 is a schematic configuration diagram of a composite focused ion beam device according to the present embodiment. FIG. 2 is a schematic cross-sectional view of the composite focused ion beam device 100.

As shown in FIGS. 1 and 2, the composite focused ion beam device 100 according to the present invention includes a vacuum chamber 13, a first ion beam irradiation system 10, a second ion beam irradiation system 20, a sample stage 16, a manipulator 17, a secondary charged particle detector 18, a transmitted charged particle detector 19, and a gas gun 11. The inside of the vacuum chamber 13 is depressurized to a predetermined vacuum degree and some or all of the above components are disposed in the vacuum chamber 13.

In the present embodiment, each of the first ion beam irradiation system 10 and the second ion beam irradiation system 20 has a focused ion beam lens barrel and irradiates a focused ion beam (a first ion beam 10A or a second ion beam 20A) to a sample (an object to be processed or an object to be observed) on a sample stage 16 disposed in the vacuum chamber 13.

As shown in FIG. 2, the first ion beam irradiation system 10 has a plasma type gas ion source 34 and an ion optical system 35. The plasma type gas ion source 34 includes, for example, a plasma generator for emitting a first ion while maintaining plasma therein, an extraction orifice for extracting the first ion from the plasma generator, and an extraction electrode for electrostatically accelerating the first ion passing the extraction orifice.

Rare gas is used in plasma gas which forms plasma in the plasma type gas ion source 34. That is, plasma gas is preferably one or plural types of gas selected from neon, argon, xenon and krypton and, among them, argon or xenon are more preferably used.

In addition, an Inductive Coupled Plasma (ICP) ion source is preferably used as the plasma type gas ion source 34, and, by this configuration, the plasma density of the ion source can be improved and the ion can be efficiently extracted.

The first ion extracted from the extraction electrode is emitted in a beam form and is focused by an ion optical operation by the ion optical system 35 such that a focused ion beam (first ion beam) 10A is irradiated to a sample Wa or a sample Wb.

The ion optical system 35 includes, for example, a condenser lens for converging an ion beam, a diaphragm for narrowing the ion beam, an aligner for adjusting an optical axis of the ion beam, an objective lens for converging the ion beam to a sample, and a deflector for scanning the ion beam on the sample, sequentially from the plasma type gas ion source 34 to the vacuum chamber 13.

The second ion beam irradiation system 20 includes a gas field ion source 21 for generating and emitting a second ion and an ion optical system 25 for converting the second ion emitted from the gas field ion source 21 into a focused ion beam (second ion beam 20A).

The ion optical system 25 has the same basic configuration as the ion optical system 35 included in the first ion beam irradiation system 10 and includes, for example, a condenser lens for converging an ion beam, a diaphragm for narrowing the ion beam, an aligner for adjusting an optical axis of the ion beam, an objective lens for converging the ion beam to a sample, and a deflector for scanning the ion beam on the sample.

Figure 3:
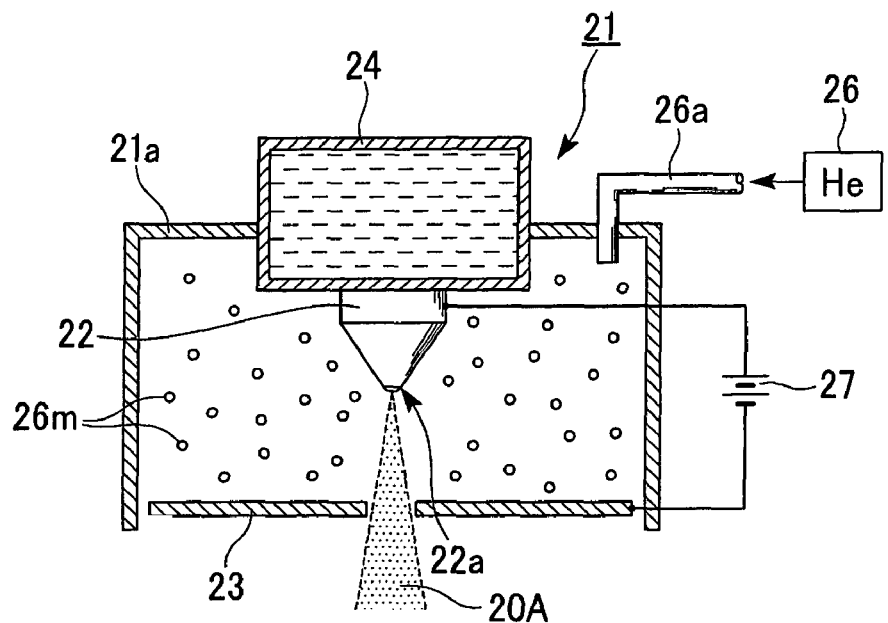
FIG. 3 is a cross-sectional view of a field emission type ion source.

FIG. 3 is a cross-sectional view of the gas field ion source 21.

As shown in FIG. 3, the gas field ion source 21 includes an ion generation chamber 21a, an emitter 22, an extraction electrode 23, and a cooling device 24. The cooling device 24 is disposed on a wall of the ion generation chamber 21a and a needle-like emitter 22 is mounted on a surface of the cooling device 24 facing the ion generation chamber 21a. The cooling device 24 cools the emitter 22 by a cooling medium such as liquid nitrogen or the like contained therein. In addition, the extraction electrode 23 having an opening 23a is disposed at a position facing a front end 22a of the emitter 22 in the vicinity of an opened end of the ion generation chamber 21a.

The inside of the ion generation chamber 21a is maintained in a desired high vacuum state using an exhauster (not shown). A gas supply source 26 is connected to the ion generation chamber 21a via a gas introduction pipe 26a and a small amount of gas (for, example, helium gas) is supplied into the ion generation chamber 21a.

In addition, the gas supplied from the gas supply source 26 to the gas field ion source 21 is not limited to helium gas and gas such as neon, argon or xenon may be used. In addition, plural types of gas may be configured to be supplied from the gas supply source 26 such that the gas type is changed according to the use of the second ion beam irradiation system 20.

The emitter 22 is a member obtained by coating a needle-like base formed of tungsten or molybdenum with noble metal such as platinum, palladium, iridium, rhodium or gold, and the front end 22a thereof is sharpened at an atomic level so as to have a pyramid shape. In addition, the emitter 22 is maintained at a low temperature of about 78 K or less by the cooling device 24 during the operation of the ion source. A voltage is applied between the emitter 22 and the extraction electrode 23 by a power source 27.

If the voltage is applied between the emitter 22 and the extraction electrode 23, a significantly large electric field is generated in the sharpened front end 22a and helium atoms 26m polarized and attracted to the emitter 22 lose electrons by tunneling at a position having a high electric field of the front end 22a so as to become helium ions (second ions) (electric field ionization). These helium ions are repulsed against the emitter 22 held at a positive potential and shoot out to the extraction electrode 23 such that the helium ions emitted from the opening 23a of the extraction electrode 23 to the ion optical system 25 configure the ion beam.

Since the front end 22a of the emitter 22 has an extremely sharpened shape and the helium ions shoot out from the front end 22a, the energy distribution width of the ion beam emitted from the gas field ion source 21 is extremely narrow and an ion beam having a small beam diameter and high luminance can be obtained, compared with the plasma type gas ion source 34 or the liquid metallic ion source.

In addition, if the voltage applied to the emitter 22 is significantly large, the constituent element (tungsten or platinum) of the emitter 22 flies toward the extraction electrode 23 together with the helium ions and thus the voltage applied to the emitter 22 is maintained at a voltage for preventing the constituent element of the emitter 22 itself from shooting out at the time of operation (at the time of ion beam radiation).

Meanwhile, the shape of the front end 22a can be adjusted by adjusting the constituent element of the emitter 22. For example, an element located at an uppermost end of the front end 22a is intentionally removed so as to widen a region for ionizing the gas such that the diameter of the ion beam can be increased.

In addition, since the emitter 22 is heated such that the noble metal element of the surface thereof is rearranged without shooting out, the sharpened shape of the front end 22a which thickens by use can be recovered.

Returning to FIGS. 1 and 2, the sample stage 16 movably supports a sample pedestal 14 and a sample holder 15. A sample Wa (for example, a semiconductor wafer or the like) is laid on the sample pedestal 14 and a fine sample Wb manufactured from the sample Wa is laid on the sample holder 15. The sample stage 16 can displace the sample pedestal 14 and the sample holder 15 by five axes. That is, an XYZ movement mechanism 16b for moving the sample pedestal 14 in an X axis and a Y axis which are parallel to a horizontal plane and are orthogonal to each other and a Z axis orthogonal to the X axis and the Y axis, a rotation mechanism 16c for rotating the sample pedestal 14 around the Z axis, and a tilt mechanism 16a for rotating the sample pedestal 14 around the X axis (or the Y axis) are included. The sample stage 16 displaces the sample pedestal 14 by the five axes such that a specific position of the sample Wa (sample Wb) becomes a position where the ion beam is irradiated.

The inside of the vacuum chamber 13 can be depressurized to a predetermined vacuum degree, and the manipulator 17, the secondary charged particle detector 18, the transmitted charged particle detector 19 and the gas gun 11 are provided in the vacuum chamber 13.

The manipulator 17 supports the sample Wb manufactured from the sample Wa. By relatively moving the manipulator 17 and the sample holder 15 in a state in which the sample Wb is supported, the sample Wb is transported from the sample pedestal 14 to the sample holder 15. During transportation, the sample stage 16 may be driven in a state in which the manipulator 17 is fixed such that the sample holder 15 is moved to a position where the sample Wb is supported, and the manipulator 17 may be moved so as to transport the sample Wb.

The secondary charged particle detector 18 detects the secondary electrons or the secondary ions generated from the sample Wa or the sample Wb when the focused ion beam is irradiated from the first ion beam irradiation system 10 or the second ion beam irradiation system 20 to the sample Wa or the sample Wb. In addition, the transmitted charged particle detector 19 detects the ions transmitted through the sample Wa or the sample Wb when the focused ion beam is irradiated from the second ion beam irradiation system 20 to the sample Wa or the sample Wb.

In this embodiment, the secondary charged particle detector 18 includes a first ion detector 18A for detecting the secondary ions generated by the irradiation of the first ions generated from the first ion beam irradiation system 10 and a second ion detector 18B for detecting the reflection ions generated from the second ion beam irradiation system and reflected by the collision of the second ions lighter than the first ions with the sample. The degree of freedom of the disposition of the first ion detector 18A is high because the secondary ions generated by the irradiation of the first ions are radiated over a wide range. In contrast, the second ion detector 18B is preferably disposed in the vicinity of the beam lens barrel of the first ion beam irradiation system 10 because the radiation angle of the reflection ions reflected by collision with the samples Wa and Wb is decided to a certain extent.

The gas gun 11 emits predetermined gas such as etching gas or deposition gas to the samples Wa and Wb. In addition, the first ion beam 10A or the second ion beam 20A is irradiated to the samples Wa and Wb while supplying the etching gas from the gas gun 11 such that the etching rate of the sample using the ion beam can be increased. Meanwhile, if the ion beam is irradiated to the samples Wa and Wb while supplying the deposition gas from the gas gun 11, it is possible to form a deposit of an insulating material or metal on the samples Wa and Wb.

The composite focused ion beam device 100 includes a control device 30 for controlling the components configuring the device. The control device 30 is connected to the first ion beam irradiation system 10, the second ion beam irradiation system 20, the secondary charged particle detector 18, the transmitted charged particle detector 19, and the sample stage 16. A display device 38 for displaying the sample Wa and the sample Wb as an image based on the output from the secondary charged particle detector 18 or the transmitted charged particle detector 19 is included.

The control device 30 comprehensively controls the composite focused ion beam device 100, converts the secondary charged particles or the transmitted charged particles detected by the secondary charged particle detector 18 or the transmitted charged particle detector 19 into a luminance signal so as to generate image data, and outputs the image data to the display device 38. Accordingly, the display device 38 can display the sample image as described above.

In addition, the control device 30 drives the sample stage 16 based on an instruction of software or input of an operator so as to adjust the position or the attitude of the sample Wa or the sample Wb. Therefore, the irradiation position or the irradiation angle of the ion beam on the sample surface can be adjusted. For example, the sample stage 16 can be driven by interlocking with the switching operation of the first ion beam irradiation system 10 and the second ion beam irradiation system 20 such that the sample Wa or the sample Wb is moved or tilted.

In the composite focused ion beam device 100 according to the present embodiment having the above configuration, the mass of the second ions (helium ions) emitted from the second ion beam irradiation system 20 is smaller than that of the first ions (argon ions or xenon ions) emitted from the first ion beam irradiation system 10. To this end, even when the second ion beam 20A is irradiated onto the sample Wa or the sample Wb, the sample will not sputter easily and an ion beam irradiation system suitable for secondary charged particle image observation of the sample Wa or the sample Wb is obtained.

In addition, in the second ion beam irradiation system 20, since a source size is 1 nm or less and the energy spread of the ion beam is 1 eV or less, the beam diameter can be narrowed to 1 nm or less. In order to obtain the beam diameter of 1 nm or less, WD should be set to 1 to 2 mm or less in order to avoid the influence of diffraction aberration in the Scanning Electron Microscope (SEM), but WD is extremely hard to set to 5 mm or less by mechanical interference between lenses in a configuration having a plurality of beam irradiation systems. In contrast, in the second ion beam 20A, since the momentum of the used helium ions is significantly larger than that of the electron used in the SEM and the de Broglie wave length is significantly small, the diffraction effect is negligibly small. Accordingly, since the diffraction aberration is negligible in the second ion beam, the small beam diameter can be obtained even when WD lengthens, and high-resolution observation and measurement of sample is possible.

In addition, in the second ion beam 20A, since the interaction volume of the sample extends from the surface in a depth direction and the spread of the sample surface in the surface direction is decreased, a sample image to which information about the position where the ion beam is irradiated is accurately applied can be obtained and thus the charge-up of the sample can be suppressed. In addition, since the momentum of the helium ions is significantly greater than that of the electrons, a larger amount of secondary electrons are emitted from the sample surface.

Accordingly, the second ion beam 20A is irradiated to the sample so as to perform the secondary charged particle image observation such that a sample image with high resolution or high contrast can be obtained.

The second ion beam irradiation system 20 can emit an ion beam having a beam diameter smaller than that of the first ion beam irradiation system 10. By using the second ion beam 20A having a small beam diameter, fine processing (etching, deposition) is possible compared with the case where the sample is processed using the first ion beam 10A.

In addition, if the second ion beam 20A is configured by the helium ions, since the ion beam is only irradiated to the sample, the sample is hardly etched, but the second ion beam 20A is irradiated to the sample while etching assistant gas is supplied from the gas gun 11 such that the sample can be processed at a practical speed. In addition, if the second ion beam 20A is configured by neon ions or argon ions having a mass larger than that of the helium ions, processing efficiency can be improved.

In the composite focused ion beam device 100 of the present embodiment, since two ion beam irradiation systems having different processing dimensions are included, the ion beam irradiation systems are selected or combined according to the use thereof. In detail, a combination in which the first ion beam irradiation system 10 having a large beam diameter is mainly used for processing and the second ion beam irradiation system 20 which has a small beam diameter and can avoid the sample sputtering is mainly used for observation, and a combination in which the first ion beam irradiation system 10 is used for rough processing of the sample and the second ion beam irradiation system 20 is used for high-precision processing may be selected.

In addition, in the composite focused ion beam device 100 of the present embodiment, a liquid metal ion source is not used in either of the two ion beam irradiation systems 10 and 20. Accordingly, the sample provided to the processing of the composite focused ion beam device 100 is not contaminated by metal ions (gallium ions or the like) and the sample can be returned to the processing again, for example, after the sample taken out from the process of manufacturing a semiconductor is inspected. Accordingly, the sample used in a random sampling inspection is not wasted.

In the present embodiment, as shown in FIG. 2, the second ion beam irradiation system 20 is disposed on the vertical upper side of the sample stage 16 so as to irradiate the second ion beam 20A to the sample Wa or the sample Wb in a vertical direction. Meanwhile, the first ion beam irradiation system 10 is disposed obliquely to the vertical direction so as to irradiate the first ion beam 10A to the sample Wa or the sample Wb in an oblique direction. In the configuration in which the second ion beam 20A formed of the helium ions is emitted along the vertical direction, high-precision stage control is facilitated at the time of observation or processing and, more particularly, desired precision of the processing using the ion beam can be obtained.

In addition, the disposition of the first ion beam irradiation system 10 and the second ion beam irradiation system 20 is not limited to that shown in FIG. 2 and various disposition forms may be employed. For example, in FIG. 2, the second ion beam irradiation system 20 may be disposed so as to obliquely irradiate the second ion beam 20A with respect to the vertical direction of the sample Wa.

Figure 4:
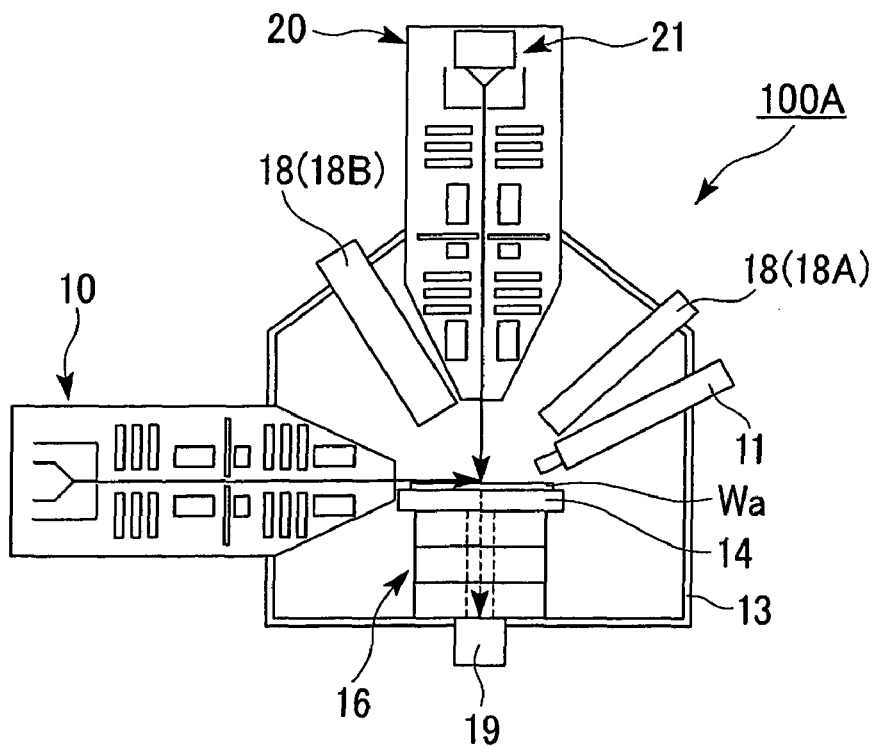
FIG. 4 is a diagram showing another configuration of the composite focused ion beam device according to the first embodiment.

FIG. 4 is a diagram showing a composite focused ion beam device 100A in which the disposition of the first and second ion beam irradiation systems 10 and 20 is changed. In the composite focused ion beam device 100A shown in FIG. 4, the second ion beam irradiation system 20 is disposed on the vertical upper side of the sample Wa and the first ion beam irradiation system 10 is disposed on the lateral side of the sample Wa. The first ion beam 10A and the second ion beam 20A are emitted so as to be substantially orthogonal to each other.

As shown in FIG. 4, the first ion beam 10A and the second ion beam 20A are disposed so as to be orthogonal to each other such that the processing of the sample using the first ion beam irradiation system 10 is performed while performing observation using the second ion beam irradiation system 20. Accordingly, the composite focused ion beam device 100A shown in FIG. 4 can be suitably used for the manufacture of a Transmission Electron Microscope (TEM) sample or the processing of a nano-order size atom probe or the like.

In addition, in the composite focused ion beam device 100A, the first ion beam irradiation system 10 and the second ion beam irradiation system 20 may be interchangeably disposed.

[Processing Observation Method and Processing Method]

Next, a processing observation method and a processing method using the composite focused ion beam device 100 according to the above embodiment will be described with reference to the drawings. The composite focused ion beam device 100 can be suitably used for section processing observation of a sample and the manufacturing and observation of a Transmission Electron Microscope (TEM) sample.

<Section Processing Observation>

FIG. 5 is a diagram showing a section processing observation method using the composite focused ion beam device 100. In addition, in FIG. 5, only a portion of the sample is shown in order to easily view the drawing.

In the processing observation method of the present example, the first ion beam irradiation system 10 is used for processing of the sample Wa and the second ion beam irradiation system 20 is used for observation of the processed sample Wa.

Figure 5A:
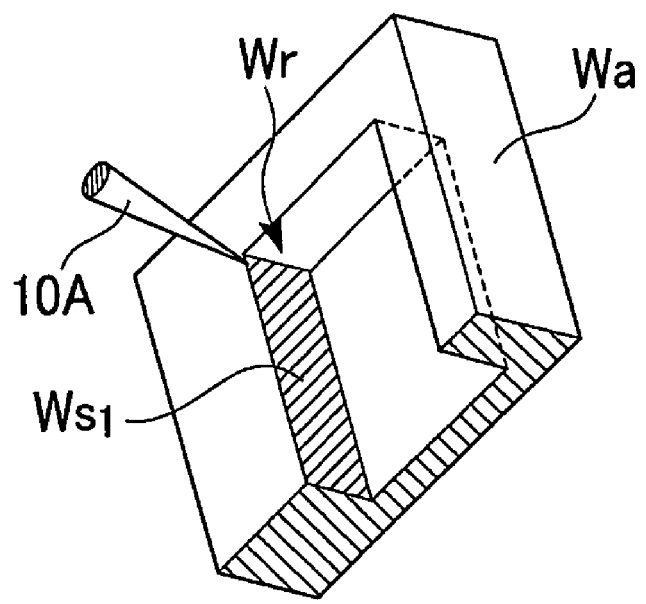
FIG. 5A is a diagram showing a section processing observation method.

First, as shown in FIG. 5A, the first ion beam 10A is scanned and irradiated to the surface of the sample Wa so as to partially remove the surface portion of the sample Wa, thereby forming a concave portion Wr having a rectangular section.

Figure 5B:
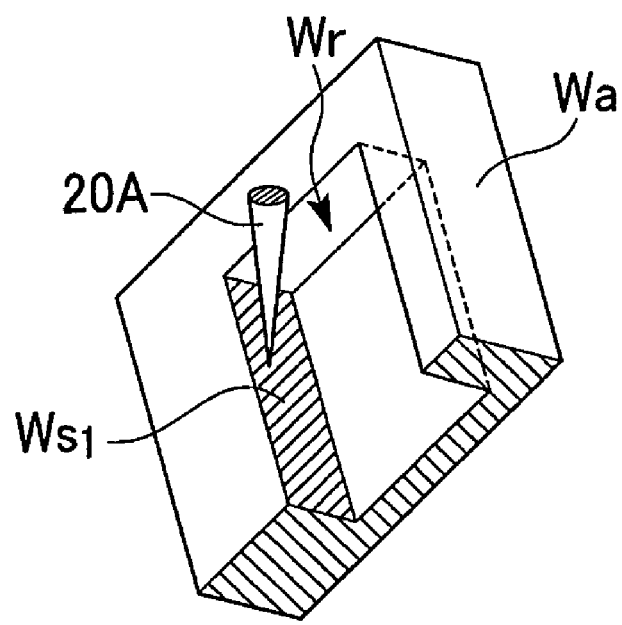
FIG. 5B is a diagram showing a section processing observation method.

In addition, as shown in FIG. 5B, the second ion beam 20A is irradiated to a surface Ws exposed as an inner wall of the formed concave portion Wr so as to detect generated secondary electrons or secondary ions by the secondary charged particle detector 18 and display a sample image on a display device 38 based on the detected result.

Here, it is possible to simultaneously perform processing by the irradiation of the first ion beam 10A to the surface of the sample Wa and observation by the irradiation of the second ion beam 20A to the surface of the sample Wa which is being processed. That is, when the first ion beam 10A and the second ion beam 20A are simultaneously irradiated to the surface of the sample Wa, secondary ions or reflection ions are generated from the sample Wa by the irradiation of the first ion beam 10A and the second ion beam 20A. The reflection ions depend on the mass or the detection angle of the incident ion beam and thus can be easily distinguished from other detected particles. To this end, by detecting only the reflection ions from the sample by the second ion detector 18B during processing, it is possible to obtain a sample image with high resolution and high contrast. The simultaneous performing of the processing and the observation of the processed portion can improve processing precision since it can be accurately checked to which degree the sample is processed in real time.

According to the processing observation method of the present example, since metallic ions are not irradiated to the sample Wa, the sample Wa cannot be contaminated by the implantation of the metallic ions and adverse effect on the sample Wa can be avoided by the processing observation. In addition, since the second ion beam irradiation system 20 for narrowing the beam diameter is used as the observation device, high-resolution observation is possible compared with the SEM.

<TEM Sample Manufacture and Observation>

FIG. 6 is a view showing a processing method of a TEM sample using the composite focused ion beam device 100. In addition, in FIG. 6, only a portion of the sample is shown in order to easily view the drawing. In addition, the irradiation direction of the ion beam is partially changed.

In the processing method of the present example, by using the first ion beam irradiation system 10 for rough processing of the sample Wa and performing finishing processing with respect to the sample after rough processing using the second ion beam irradiation system 20, a sample Wb which is a TEM sample is obtained.

Figure 6A:
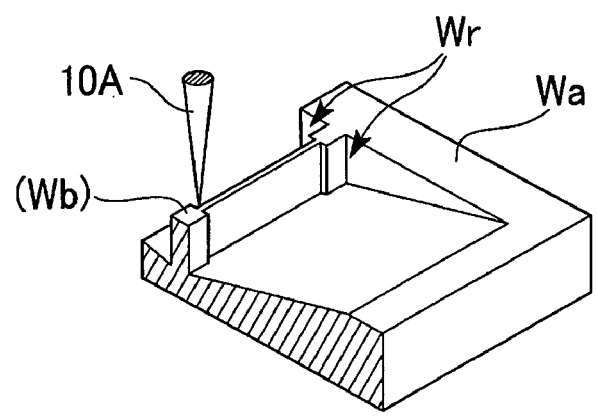
FIG. 6A is a diagram showing a TEM sample manufacturing and observation method.

First, as shown in FIG. 6A, the first ion beam 10A is scanned and irradiated to the surface of the sample Wa so as to perform partial removal and concave portions Wr and Wr having a slope shape are formed in a bottom surface at both sides of a portion which becomes the sample Wb which is the TEM sample.

Figure 6B:
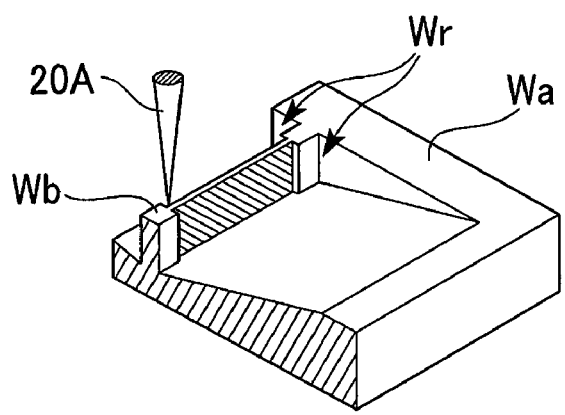
FIG. 6B is a diagram showing a TEM sample manufacturing and observation method.

Next, as shown in FIG. 6B, the second ion beam 20A is irradiated to the sample so as to perform finishing processing of a portion which becomes an observed region of the sample Wb. At this time, gas assisted etching or gas assisted deposition using the gas gun 11 is preferably performed. The use of the gas gun 11 can improve the processing speed of the etching and the deposition and efficiently manufacture the sample Wb.

Thereafter, since the sample Wb is detached from the sample Wa in a state of being supported by the manipulator 17, the sample Wb as the TEM sample can be obtained.

According to this processing method, at the time of the manufacture of the TEM sample, since the first ion beam irradiation system 10 is used for the rough processing of the periphery of the portion which becomes the sample Wb, it is possible to rapidly process a relatively wide region. In addition, since the second ion beam irradiation system 20 is used for the finishing processing of the thin-film portion which is the observed region of the sample Wb, it is possible to perform the finishing processing of a fine portion with high precision. In addition, since the metallic ions are not irradiated to the samples Wa and Wb, it is possible to avoid an adverse effect on the samples due to the implantation of the metallic ions.

Figure 6C:
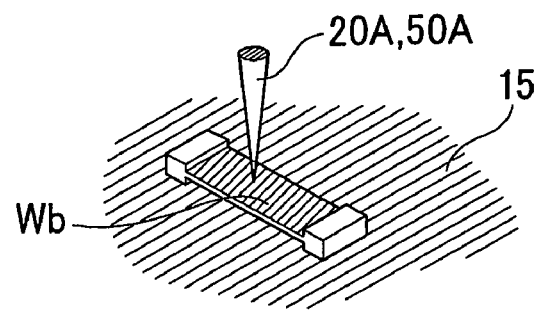
FIG. 6C is a diagram showing a TEM sample manufacturing and observation method.

In addition, in the composite focused ion beam device 100 of the present invention, the observation of the manufactured sample Wb may be performed. In this case, as shown in FIG. 6C, the detached sample Wb is moved to the sample holder 15 by the manipulator 17. Then, the second ion beam 20A is irradiated to the sample Wb and the transmitted ions are detected by the transmitted charged particle detector 19. Therefore, a sample image can be displayed on the display device 38 based on the detected result of the transmitted charged particle detector 19.

In the processing observation method of the present example, the manufacture of the sample Wb shown in FIG. 6A and FIG. 6B may be performed using only the first ion beam irradiation system 10 or the second ion beam irradiation system 20. In addition, a method of using only the first ion beam irradiation system 10 as the processing device and using the second ion beam irradiation system 20 as the observation device of the manufactured sample Wb may be employed.

In the processing using the second ion beam 20A, since the beam diameter is narrowed as compared with the first ion beam 10A, it is possible to concentrically irradiate the beam to a portion to be cut. To this end, high-precision processing which cannot be obtained in the processing by the irradiation of the first ion beam 10A is possible.

Figure 7:
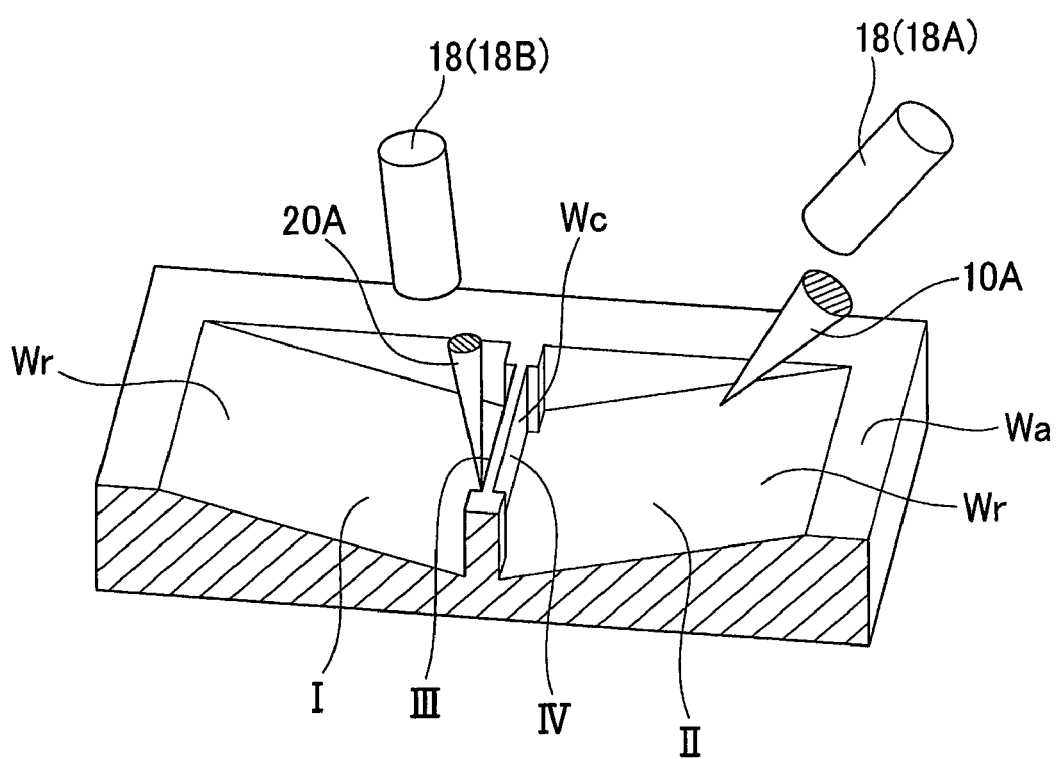
FIG. 7 is a diagram showing a TEM sample manufacturing method which is one type of processing method.

FIG. 7 is a diagram showing a procedure of manufacturing a TEM sample. Here, first, a concave portion Wr (denoted by I in the drawing) having a slope shape at the left side of FIG. 7 is removed by irradiating the first ion beam 10A. Next, a concave portion Wr (denoted by II in the drawing) having a slope shape at the right side of FIG. 7 is removed by irradiating the first ion beam. Simultaneously, a portion (denoted by III in the drawing) adjacent to a portion Wc which becomes the TEM sample of the concave portion Wr having the slope shape at the removed left side is removed by irradiating the second ion beam 20A. Next, a portion (denoted by IV in the drawing) adjacent to the portion Wc which becomes the TEM sample of the concave portion Wr having the slope shape at the removed right side is removed by irradiating the second ion beam 20A.

That is, in this TEM sample manufacturing method, in second processing, rough processing of removing the concave portion Wr (denoted by II in the drawing) having the slope shape at the right side and finishing processing of removing the portion adjacent to the portion Wc which becomes the TEM sample of the concave portion Wr having the slope shape at the removed left side are simultaneously performed and thus processing efficiency can be improved. At this time, there may be a problem that the material removed when the rough processing is performed is reattached to the finishing processed portion. However, since the portion Wc which becomes the TEM sample is present between both the processed regions, such a problem does not easily occur. When the rough processing and the finishing processing are simultaneously performed, the secondary ions generated by the irradiation of the first ions can be detected by the first ion detector 18A and the reflection ions reflected by collision of the second ions with the sample can be detected by the second ion detector 18B, the processed portions can be simultaneously monitored. Even in this case, processing efficiency can be improved.

Second Embodiment

Next, a second embodiment of the present invention will be described with reference to FIGS. 8 and 9.

Figure 8:
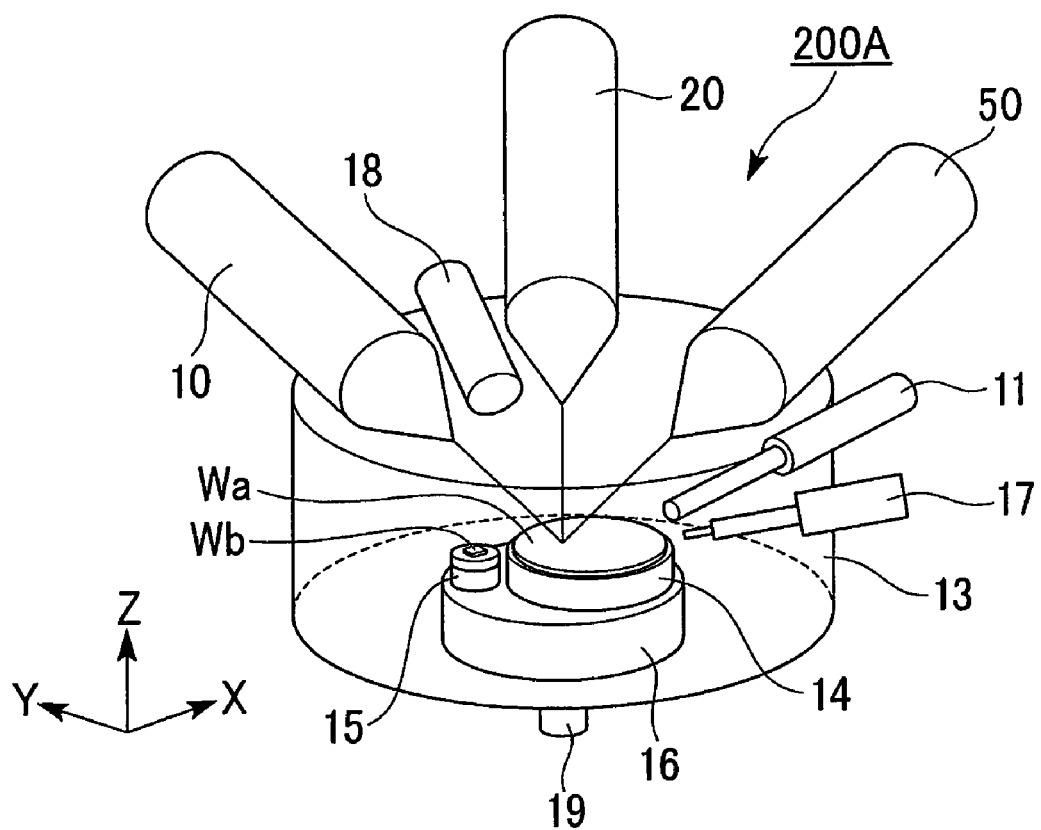
FIG. 8 is a schematic configuration diagram of a composite focused ion beam device according to a first configuration example of a second embodiment.
Figure 9:
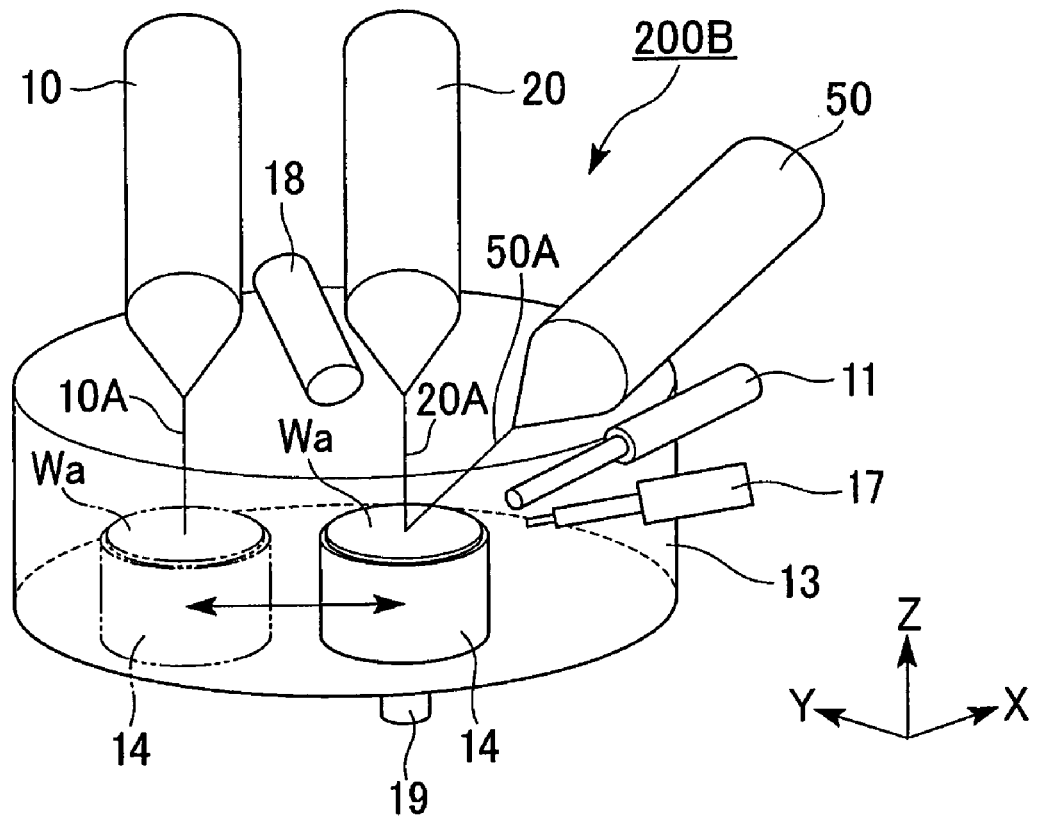
FIG. 9 is a schematic configuration diagram of a composite focused ion beam device according to a second configuration example of a second embodiment.

FIG. 8 is a schematic configuration diagram of a composite focused ion beam device 200A according to a first configuration example of the present embodiment and FIG. 9 is a schematic configuration diagram of a composite focused ion beam device 200B according to a second configuration example.

In addition, in FIGS. 8 and 9, the same components as FIGS. 1 to 3 are denoted by the same reference numerals and detailed description thereof will be omitted.

First, the composite focused ion beam device 200A according to the first configuration example shown in FIG. 8 includes an electron beam irradiation system 50 in addition to the first ion beam irradiation system 10 and the second ion beam irradiation system 20. The electron beam irradiation system 50 functions as a Scanning Electron Microscope (SEM) lens barrel for irradiating an electron beam to the sample Wa. Accordingly, the composite focused ion beam device 200A irradiates the first ion beam 10A and the second ion beam 20A emitted from the first and second ion beam irradiation systems 10 and 20 to the sample Wa and performs sample image observation using the electron beam irradiation system 50 which is the SEM lens barrel. As the electron beam irradiation system 50, a known configuration may be employed.

In the composite focused ion beam device 200A, in the first ion beam irradiation system 10, the second ion beam irradiation system 20 and the electron beam irradiation system 50, the lens barrels are disposed such that the ion beam and the electron beam can be irradiated to the same place on the sample Wa.

Next, the composite focused ion beam device 200B according to the second configuration example shown in FIG. 9 is similar to the composite focused ion beam device 200A according to the first configuration example in which the electron beam irradiation system 50 is included in addition to the first ion beam irradiation system 10 and the second ion beam irradiation system 20. However, in the composite focused ion beam device 200B, the lens barrels are disposed such that the irradiation directions of the first ion beam 10A and the second ion beam 20A are substantially parallel to each other.

In addition, the sample pedestal 14 can be moved freely in a horizontal direction. By this configuration, the sample Wa laid on the sample pedestal 14 is moved between a position where the first ion beam 10A is irradiated and a position where the second ion beam 20A is irradiated.

In addition, the electron beam irradiation system 50 irradiates an electron beam 50A to the sample Wa obliquely to a vertical direction. In addition, the electron beam irradiation system 50 is disposed in the vicinity of the second ion beam irradiation system 20 so as to irradiate the electron beam 50A to the same position on the sample Wa to which the second ion beam 20A is irradiated.

The composite focused ion beam devices 200A and 200B according to the present embodiment having the above configurations can perform the sample processing observation and processing using the first ion beam irradiation system 10 and the second ion beam irradiation system 20, similar to the composite focused ion beam device 100 according to the first embodiment.

In addition, since the electron beam irradiation system 50 which is the SEM lens barrel is included in addition to the first ion beam irradiation system 10 and the second ion beam irradiation system 20, in particular, in the observation of the sample, it is possible to obtain a composite focused ion beam device which can employ more various observation forms than the first embodiment.

As described above, in the composite focused ion beam device according to the present invention, the second ion beam 20A is irradiated from the second ion beam irradiation system 20 to the sample and the generated secondary ions are detected such that a sample image (SIM image) can be obtained. However, in the present embodiment, the electron beam 50A is irradiated from the electron beam irradiation system 50 to the sample such that a secondary electron image (SEM image) can be obtained. Since the SEM image and the SIM image are different in contrast, if they are selected according to the structure of the sample or the like, higher-precision processing observation is possible. For example, a multi-layer insulating film or the like is seen as black in the SIM image and is hard to observe, but a high-contrast image can be seen by switching to the SEM image.

In addition, since the second ion beam irradiation system 20 is used as an ion beam irradiation system for the fine processing of the sample, the high-speed high-precision processing using the first ion beam irradiation system 10 and the second ion beam irradiation system 20 can be performed while checking the finishing state by observation using the electron beam irradiation system 50.

[Processing Observation Method and Processing Method]

Hereinafter, a processing observation method and a processing method using the composite focused ion beam devices 200A and 200B according to the above embodiment will be described with reference to the drawings. The composite focused ion beam devices 200A and 200B can be suitably used for continuous section processing observation of a sample and the manufacturing and observation of a Transmission Electron Microscope (TEM) sample.

<Section Processing Observation>

FIG. 10 is a diagram showing a continuous section processing observation method using the composite focused ion beam device 200A or 200B. In addition, in FIG. 10, only a portion of the sample is shown in order to easily view the drawing. In order to simplify the description, the irradiation direction of the ion beam is partially changed.

In the processing observation method of the present example, the first ion beam irradiation system 10 and the second ion beam irradiation system 20 are used for processing the sample Wa and the electron beam irradiation system 50 is used for observation of the processed sample Wa.

Figure 10A:
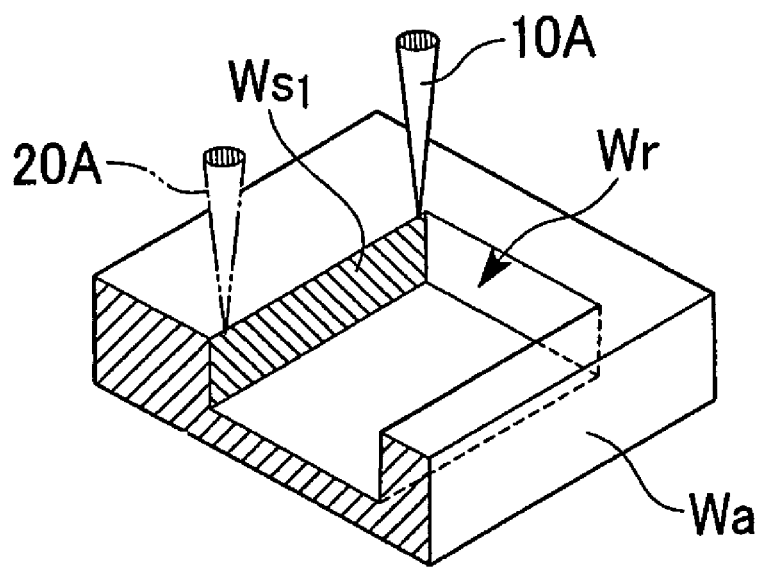
FIG. 10A is a diagram showing a continuous section processing observation method.

(1) The case where the composite focused ion beam device 200A according to the first configuration example is used First, as shown in FIG. 10A, the first ion beam 10A is scanned and irradiated to the surface of the sample Wa so as to partially remove the surface portion of the sample Wa, thereby forming a concave portion Wr having a rectangular section. By the processing using the first ion beam 10A, a first section Ws1 which is an observation object is exposed as an inner wall of the concave portion Wr.

Next, the second ion beam 20A is irradiated to the sample Wa such that the finishing processing of the first section Ws1 which is the observation object is performed. In the composite focused ion beam device 200A, since the first ion beam 10A and the second ion beam 20A can be irradiated to the same position of the sample Wa, the processing using the first ion beam 10A and the second ion beam 20A can be continuously performed simply by changing the angle of the sample Wa.

Figure 10B:
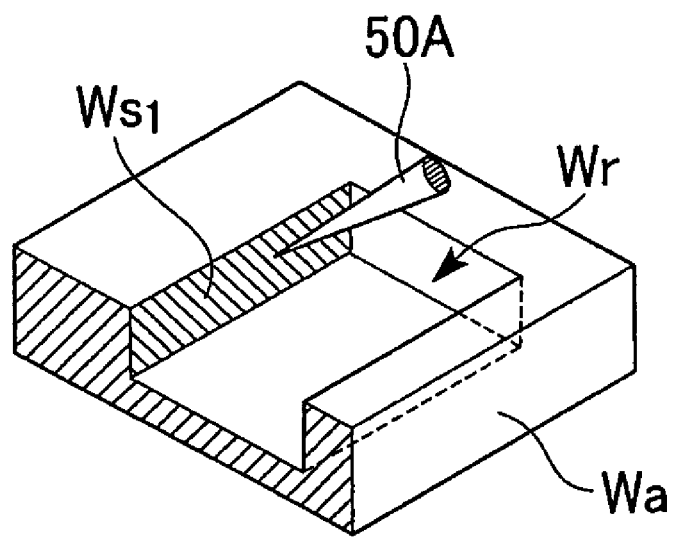
FIG. 10B is a diagram showing a continuous section processing observation method.

In addition, as shown in FIG. 10B, the electron beam 50A is irradiated to the first section Ws1 which is subjected to the finishing processing such that the secondary electrons or secondary ions generated from the sample are detected by the secondary charged particle detector 18 and a sample image can be displayed on the display device 38 based on the detected result.

Figure 10C:
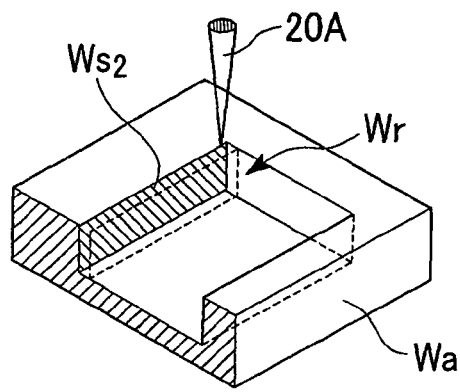
FIG. 10C is a diagram showing a continuous section processing observation method.

Next, as shown in FIG. 10C, the second ion beam 20A is irradiated in the vicinity of the first section Ws1 of the sample Wa. Therefore, a portion including the first section Ws1 is selectively removed and a second section Ws2 at the inside of the first section Ws1 is exposed. In this process, since the sample is processed using the second ion beam 20A for narrowing the beam diameter, it is possible to process the sample with high precision and easily obtain a section having a desired state.

In the process, when the second ion beam 20A is irradiated from the gas gun 11 while supplying assistant etching gas, it is possible to efficiently process the sample.

Figure 10D:
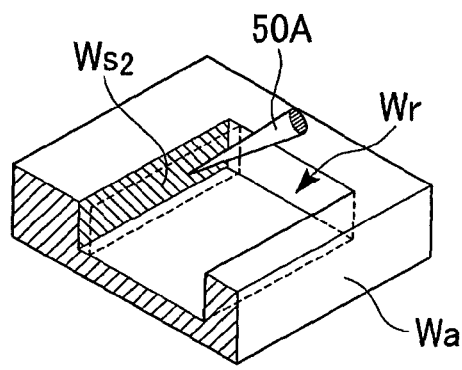
FIG. 10D is a diagram showing a continuous section processing observation method.

As shown in FIG. 10D, the electron beam 50A is irradiated to the second section Ws2 such that the secondary electrons or secondary ions generated from the sample are detected by the secondary charged particle detector 18 and a sample image can be displayed on the display device 38 based on the detected result.

Figure 10E:
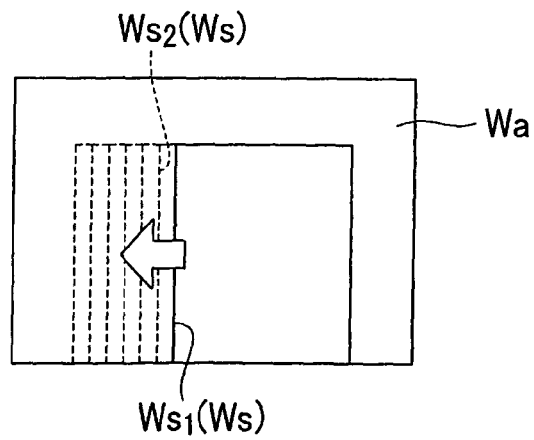
FIG. 10E is a diagram showing a continuous section processing observation method.

Thereafter, since the processes shown in FIGS. 10C and 10D are repeatedly performed, as shown in FIG. 10E, sections of desired positions of the sample Wa can be continuously observed.

(2) The case where the composite focused ion beam device 200B according to the second configuration example is used Even in the case where the composite focused ion beam device 200B according to the second configuration example is used, first, as shown in FIG. 10A, a concave portion Wr is formed in the sample Wa. That is, the sample pedestal 14 which supports the sample Wa is disposed at the front of the first ion beam irradiation system 10 and the first ion beam 10A is irradiated to the sample Wa so as to form the concave portion Wr (rough processing).

If the concave portion Wr is formed, next, the sample pedestal 14 is moved to the front of the second ion beam irradiation system 20. As shown in FIG. 10A, the second ion beam 20A is irradiated to the first section Ws1 exposed as the inner wall of the concave portion Wr and the finishing processing of the first section Ws1 is performed. Therefore, the first section Ws1 as an observation object is obtained.

As shown in FIG. 10B, the electron beam 50A is irradiated to the first section Ws1 subjected to the finishing processing such that the secondary electrons or secondary ions generated from the sample are detected by the secondary charged particle detector 18 and a sample image can be displayed on the display device 38 based on the detected result. In the composite focused ion beam device 200B according to the second configuration example, since the electron beam irradiation system 50 is disposed in the vicinity of the second ion beam irradiation system 20 and the electron beam 50A can be irradiated to the same position as the second ion beam 20A, the finishing processing of the first section Ws1 and the SEM observation can be continuously performed without moving the sample pedestal 14.

Next, as shown in FIG. 10C, the second ion beam 20A is irradiated in the vicinity of the first section Ws1 of the sample Wa. Therefore, a portion including the first section Ws1 is selectively removed and a second section Ws2 at the inside of the first section Ws1 is exposed. In this process, since the sample is processed using the second ion beam 20A for narrowing the beam diameter, it is possible to process the sample with high precision and easily obtain a section having a desired state. In the process, when the second ion beam 20A is irradiated from the gas gun 11 while supplying assistant etching gas, it is possible to efficiently process the sample.

As shown in FIG. 10D, the electron beam 50A is irradiated to the second section Ws2 such that the secondary electrons or secondary ions generated from the sample are detected by the secondary charged particle detector 18 and a sample image can be displayed on the display device 38 based on the detected result.

Thereafter, since the processes shown in FIGS. 10C and 10D are repeatedly performed, as shown in FIG. 10E, sections of desired positions of the sample Wa can be continuously observed.

In the processing observation of the present example, since the rough processing of the sample Wa is performed using the first ion beam irradiation system 10 and the finishing processing of the first section Ws1 is performed using the second ion beam irradiation system 20, the first section Ws1 which is an observation object can be processed with high precision and a high-quality sample section image can be obtained.

In the processing of the sections after the second section Ws2, since the processing is performed using the second ion beam irradiation system 20, it is possible to perform section processing with high precision without moving the sample Wa. Accordingly, it is possible to obtain a high-precision sample image in all sample sections.

According to the processing observation method of the present example, since the metallic ions are not irradiated to the sample Wa, the sample Wa cannot be contaminated by the implantation of the metallic ions and adverse effect on the sample Wa can be avoided by the processing observation.

<TEM Sample Manufacture and Observation>

The composite focused ion beam devices 200A and 200B according to the second embodiment can be suitably used for a processing method such as manufacture of a TEM sample or formation of a fine structure.

Even when the composite focused ion beam devices 200A and 200B according to the present embodiment are used, it is possible to obtain a sample Wb which is a TEM sample by the creation method shown in FIG. 6. That is, the rough processing of the sample Wa is performed using the first ion beam irradiation system 10 and the finishing processing is performed using the second ion beam irradiation system 20 such that the sample Wb of the thin film can be manufactured.

In addition, in the composite focused ion beam devices 200A and 200B according to the present embodiment, since the electron beam irradiation system 50 is included, the observation of the sample Wb detached from the sample Wa can be continuously performed. That is, as shown in FIG. 6C, the electron beam 50A is irradiated to the sample Wb which is moved to and laid on the sample holder 15 (not shown in FIGS. 8 and 9) by the manipulator 17 and the transmitted electrons are detected by the transmitted charged particle detector 19 such that a transmitted electron image of the sample Wb can be obtained.

<Formation of Fine Structure>

The composite focused ion beam devices 200A and 200B according to the present embodiment are applicable to a method (processing method) of forming a fine structure such as an atom probe.

The composite focused ion beam devices 200A and 200B according to the present embodiment include the first ion beam irradiation system 10 and the second ion beam irradiation system 20 which can be used as the processing device and includes the electron beam irradiation system 50 which can be used as the observation device. Accordingly, processing can be performed by adequately selecting the first ion beam irradiation system 10 and the second ion beam irradiation system 20 according to the processing dimension and processing can be performed while checking the finishing state of the fine structure by the electron beam irradiation system 50.

Accordingly, according to the method of forming the fine structure of the present example, it is possible to efficiently form a fine structure having a desired shape with high precision.

INDUSTRIAL APPLICABILITY

The present invention relates to a composite focused ion beam device. According to the composite focused ion beam device of the present invention, since a first ion beam irradiation system having a plasma type gas ion source for generating a first ion and a second ion beam irradiation system including a gas field ion source for generating a second ion are included and a beam diameter of the second ion beam emitted from the second ion beam irradiation system is smaller than that of the first ion beam emitted from the first ion beam irradiation system, it is possible to perform super-high-resolution SIM observation compared with the related art and process a sample without contamination.

The invention claimed is:

1. A composite focused ion beam device comprising:
a first ion beam irradiation system that irradiates a first ion beam for processing a sample, the first ion beam irradiation system having a plasma type gas ion source that generates first ions for forming the first ion beam, the first ions each having a first mass; and
a second ion beam irradiation system that irradiates a second ion beam for processing or observing the sample, the second ion beam irradiation system having a gas field ion source that generates second ions for forming the second ion beam, the second ions each having a second mass smaller than that of the first mass.

2. A processing and observation method of a sample, the method comprising the steps of:
processing a sample by irradiating the sample with a first ion beam from a first ion beam irradiation system having a plasma type gas ion source that generates first ions for forming the first ion beam, the first ions each having a first mass; and
observing the sample by irradiating the sample with a second ion beam from a second ion beam irradiation system having a gas field ion source that generates second ions for forming the second ion beam, the second ions each having a second mass smaller than the first mass.

3. A processing and observation method according to claim 2; wherein the first and second ion beams are simultaneously irradiated on the sample.

4. A processing method of a sample, the method comprising the steps of:
performing rough processing of a sample by irradiating the sample with a first ion beam from a first ion beam irradiation system having a plasma type gas ion source that generates first ions for forming the first ion beam, the first ions each having a first mass; and
performing finishing processing of the sample by irradiating the sample with a second ion beam from a second ion beam irradiation system having a gas field ion source that generates second ions for forming the second ion beam, the second ions each having a second mass smaller than that of the first mass.

5. A composite focused ion beam device according to claim 1; further comprising an electron beam irradiation system for observing the sample.

6. A composite focused ion beam device according to claim 1; wherein the first ion beam irradiation system and the second ion beam irradiation system are configured to irradiate the first ion beam and the second ion beam, respectively, so as to cross each other at an acute angle.

7. A composite focused ion beam device according to claim 6; further comprising a sample pedestal for supporting the sample irradiated by the first and second ion beams, the second ion beam irradiation system being disposed on an upper side of the sample pedestal and the first ion beam irradiation system being positioned obliquely to a vertical direction of the second ion beam irradiation system.

8. A composite focused ion beam device according to claim 1; wherein the first ion beam irradiation system and the second ion beam irradiation system are configured to irradiate the first ion beam and the second ion beam, respectively, so as to be substantially orthogonal to each other.

9. A composite focused ion beam device according to claim 1; wherein the first ion beam irradiation system and the second ion beam irradiation system are configured to irradiate the first ion beam and the second ion beam, respectively, so as to be substantially parallel to each other.

10. A composite focused ion beam device according to claim 1; wherein the second ion is a helium ion.

11. A composite focused ion beam device according to claim 1; the first ion is one or more of rare gas ions selected from neon, argon, xenon and krypton.

12. A composite focused ion beam device according to claim 1; further comprising: a detection device for detecting at least one of a secondary charged particle generated or reflected from the sample by the irradiation of the first ion beam or the second ion beam, and a charged particle transmitted through the sample; and an image display device for displaying an image of the sample based on an output of the detection device.

13. A composite focused ion beam device according to claim 12; wherein the detection device comprises at least one of an electron detector, an ion detector, and a transmitted charged particle detector.

14. A processing and observation method according to claim 2; wherein the sample is irradiated with the first ion beam and the second ion beam so that the first and second ion beams cross each other at an acute angle.

15. A processing and observation method according to claim 2; wherein the sample is irradiated with the first ion beam and the second ion beam so that the first and second ion beams are substantially orthogonal to each other.

16. A processing and observation method according to claim 2; wherein the sample is irradiated with the first ion beam and the second ion beam so that the first and second ion beams are substantially parallel to each other.

17. A processing method according to claim 4; wherein the first and second ion beams are simultaneously irradiated on the sample.

18. A processing method according to claim 4; wherein the sample is irradiated with the first ion beam and the second ion beam so that the first and second ion beams cross each other at an acute angle.

19. A processing method according to claim 4; wherein the sample is irradiated with the first ion beam and the second ion beam so that the first and second ion beams are substantially orthogonal to each other.

20. A processing method according to claim 4; wherein the sample is irradiated with the first ion beam and the second ion beam so that the first and second ion beams are substantially parallel to each other.

* * * * *